US011253334B2

(12) United States Patent
Mueller et al.

(10) Patent No.: US 11,253,334 B2
(45) Date of Patent: Feb. 22, 2022

(54) MOUNT FOR A DIGITAL SURGICAL MICROSCOPE WITH POSITION CORRECTION

(71) Applicant: Carl Zeiss Meditec AG, Jena (DE)

(72) Inventors: Andre Mueller, Koenigsbronn-Zang (DE); Daniel Kolster, Oberkochen (DE); Axel Lorenz, Meissen (DE); Joachim Steffen, Westhausen (DE)

(73) Assignee: Carl Zeiss Meditec AG, Jena (DE)

( * ) Notice: Subject to any disclaimer, the term of this patent is extended or adjusted under 35 U.S.C. 154(b) by 0 days.

(21) Appl. No.: 17/119,916

(22) Filed: Dec. 11, 2020

(65) Prior Publication Data

US 2021/0177539 A1      Jun. 17, 2021

(30) Foreign Application Priority Data

Dec. 13, 2019    (DE) .................... 10 2019 134 329.1

(51) Int. Cl.
*A61B 90/25*      (2016.01)
*A61B 90/00*      (2016.01)

(52) U.S. Cl.
CPC ............ *A61B 90/25* (2016.02); *A61B 90/361* (2016.02)

(58) Field of Classification Search
CPC ............................. A61B 90/25; A61B 90/361
See application file for complete search history.

(56) References Cited

U.S. PATENT DOCUMENTS 5,748,366 A * 5/1998 Yasunaga ........... G02B 21/0012
                                                      359/363
6,982,827 B2   1/2006  Mora
(Continued)

FOREIGN PATENT DOCUMENTS

DE         103 35 644 B3    12/2005
DE         600 23 015 T2     7/2006
(Continued)

OTHER PUBLICATIONS

"Usability of a Robotic Surgical Microscope"—Markus Finke and Achim Schweikard; Proceedings of the 2010 3rd IEEE RAS & EMBS; International Conference on Biomedical Robotics and Biomechatronics, The University of Tokyo, Tokyo, Japan, Sep. 26-29, 2010 (Year: 2010).*

(Continued)

*Primary Examiner* — Mainul Hasan
(74) *Attorney, Agent, or Firm* — Walter Ottesen, P.A.

(57) ABSTRACT

A mount for an optical apparatus having an image recording unit and an image rendering unit includes a first securing device for the recording unit, a second securing device for the rendering unit, and a connecting rail interconnecting the securing devices. The connecting rail is arranged so as to be displaceable in the y-direction in relation to the second securing device via a linear actuator. The first securing device includes a rotation device arranged so as to be rotatable about an axis of rotation extending in the x-direction. The mount includes a controller which is configured to displace the connecting rail in the y-direction in relation to the second securing device via the actuator when the first securing device is rotated about the tilt axis such that the distance between the focal point and the second securing device is kept constant within a certain interval.

13 Claims, 8 Drawing Sheets

(56) References Cited

U.S. PATENT DOCUMENTS

| | | | |
|---|---|---|---|
| 7,190,513 B2 | 3/2007 | Obrebski et al. | |
| 2005/0063047 A1* | 3/2005 | Obrebski | G02B 21/24 |
| | | | 359/368 |
| 2009/0218456 A1* | 9/2009 | Metelski | F16M 11/2085 |
| | | | 248/157 |
| 2011/0313294 A1* | 12/2011 | De Roode | A61M 5/427 |
| | | | 600/473 |
| 2015/0297311 A1* | 10/2015 | Tesar | A61B 90/37 |
| | | | 600/411 |
| 2015/0346473 A1* | 12/2015 | Ernsperger | G02B 21/0012 |
| | | | 348/79 |
| 2017/0176704 A1* | 6/2017 | Hirose | G02B 21/362 |
| 2018/0168767 A1* | 6/2018 | Hirose | A61B 90/25 |
| 2018/0263723 A1* | 9/2018 | Beaumont | A61B 90/50 |
| 2018/0368656 A1* | 12/2018 | Austin | A61B 90/20 |
| 2020/0064615 A1* | 2/2020 | Ishikawa | A61B 90/25 |

FOREIGN PATENT DOCUMENTS

| | | |
|---|---|---|
| DE | 603 05 413 T2 | 12/2006 |
| EP | 1 420 280 B1 | 5/2004 |
| WO | 2010/059045 A1 | 5/2020 |

OTHER PUBLICATIONS

English translation and Office action of the German Patent Office dated Sep. 26, 2020 in German patent application 10 2019 134 329.1 on which the claim of priority is based.

\* cited by examiner

MOUNT FOR A DIGITAL SURGICAL MICROSCOPE WITH POSITION CORRECTION

CROSS REFERENCE TO RELATED APPLICATION

This application claims priority of German patent application no. 10 2019 134 329.1, filed Dec. 13, 2019, the entire content of which is incorporated herein by reference.

FIELD OF THE INVENTION

The present disclosure relates to a mount for an optical apparatus including an image recording unit and an image rendering unit. The disclosure moreover relates to an optical apparatus, in particular a surgical microscope, and a method for operating an optical apparatus according to the disclosure.

BACKGROUND OF THE INVENTION

In microsurgery and, specifically, in ophthalmology, eyepieces of the microscope for observing the operating field are being replaced ever more frequently by two video cameras and a stereoscopic screen. In the process, the video cameras record the operating field through the imaging optical unit of the microscope and the stereoscopic screen or a digital eyepiece displays the recorded images. These digital microscopes, which are also referred to as digiscopes, are advantageous in that they provide ergonomically improved conditions for the surgeon, multifaceted options for digital image processing and augmenting the image, and improved options for the training of future surgeons. However, the 3D impression of a 3D screen is only optimal at a certain relative spatial position, that is, at a certain distance and certain angle in relation to the observer. Therefore, the distance and the observation angle between surgeon and image rendering unit, that is, the screen or the eyepiece, and the lateral and vertical angles (panning and tilting) of the screen with respect to the viewing direction of the observer should be maintained as optimally as possible while the screen or the digital eyepiece is in use.

In principle, the provision of compact digital surgical microscopes distinguished by great operating comfort while taking account of the ergonomics is sought after. Digital surgical microscopes usually include a stand, a mount, an image recording unit and a compact image rendering unit, for example a 3D monitor or a digital eyepiece. Here, the image recording unit and the image rendering unit are usually placed in relation to one another by way of a mechanical connection. This allows the user to set up an optimized arrangement in respect of the observation, that is, in particular, in view of the distance and the observation angle with respect to the image rendering unit and in respect of the ergonomics, that is, the position of the user, in particular the surgeon, and in view of the focus, in particular the body part of the patient to be operated on. Furthermore, depending on the working distance of the image recording unit, an optimal distance of the same from the patient may have to be ensured for a proper image capture. In the case of the objectives with a fixed focal length used in ophthalmology, the working distance, that is, the distance between the image recording unit and the operating field, generally is the focal length of the main objective used, for example.

Setting the desired arrangement between the operator, in particular the surgeon, the operating field, in particular the patient, the image recording unit and the image rendering unit is implemented in preparatory fashion at the start of each operation by a manipulation on the operating chair used by the surgeon, on the operating couch of the patient and the stand of the surgical microscope, via which a common position of the image recording unit and the image rendering unit is defined. Additionally, the observation field can still be optimized in respect of the optical quality by fine positioning of the image recording unit. By way of example, such fine positioning can be implemented by a horizontal movement of the image recording unit, for example in an xy-plane for adjusting the image center, and/or a movement of the image recording unit along the optical axis for setting the focus. As a rule, these movements are small and have no influence, or only a very small influence, on the ergonomics, the observation direction and the observation angle of the image rendering unit used.

It is advantageous if no changes are made on the operating chair, the operating couch and on the stand, in particular the stand settings, during a surgical intervention because this interrupts the work of the surgeon and increases risks during an operation. By way of example, the aforementioned alterations may be accompanied by unsterile control, may cause a collision potential and may, overall, have a negative effect on a delicate operation. Fine positioning of the image recording unit for altering or correcting the image center or the relative focal position is carried out in motorized fashion as a rule, possibly even in automated fashion, and it is consequently also possible, within the scope of restricted operation and with only little potential of disturbance, during the operation in a manner initiated by the surgeon, for example initiated by way of a foot switch.

In most interventions in ophthalmic microsurgery, the observation is from above, with a vertically arranged optical axis of the image recording device. In some cases, a tilt of the optical axis about a horizontal axis is desirable. To this end, the system is complemented, as a rule, by a corresponding tilt apparatus, which facilitates the tilt of the image recording unit over a restricted range relative to the remainder of the system.

Since the placement of the axis of rotation about which the image recording unit is rotated during the tilting procedure does not, as a rule, extend through the point of intersection of focal plane and optical axis, the tilt yields a displacement of the image section, quite significant in part, and defocusing. When the tilt is changed, the image recording unit must be repositioned above the patient by manipulation of the stand axes and the image center and the focus must subsequently be finely repositioned. In some operating situations, the temporary alteration of the tilt angle, in particular under sterile conditions, is desired or required during the surgical intervention. Even if the tilt is carried out in motor-driven fashion, the operating procedure is nevertheless disturbed or at least interrupted by the large correction movements by way of the stand. If, as is frequently the case, the image recording unit and the image rendering unit are secured to a common stand, the position of the image rendering unit may also change, significantly in part, when the image recording unit is tilted and hence there may be a change in the observation, in particular in the distance and the observation angle, and the ergonomics might be negatively affected, for example as a result of an inclination of the observation axis or the altered observation distance. This situation is explained in more detail and in exemplary fashion further below on the basis of FIG. 1.

The document DE 600 23 015 T2 describes an adapter for a microscope camera with control motors.

SUMMARY OF THE INVENTION

It is an object of the present invention to make available a mount for an optical apparatus having an image recording unit and an image rendering unit, which optical apparatus advantageously counteracts the aforementioned disadvantages in conjunction with the tilt of the image recording unit.

The aforementioned object can, for example, be achieved by a mount for an optical apparatus having an image recording unit and an image rendering unit. The mount includes: a connecting rail extending in a y-direction; a first securing device for an image recording unit and a second securing device for an image rendering unit, wherein the first securing device and the second securing device are mechanically interconnected via the connecting rail; the first securing device and the second securing device being arranged in succession in the y-direction; the connecting rail being arranged so as to be displaceable in the y-direction in relation to the second securing device; a linear actuator configured to displace the connecting rail in the y-direction in relation to the second securing device; the first securing device including a rotation device; the rotation device being arranged so as to be rotatable about an axis of rotation extending in an x-direction, wherein the x-direction extends perpendicular to the y-direction; the rotation device being configured to be rotated about a tilt axis extending in the x-direction by way of a rotation about the axis of rotation and a translation of the connecting rail, wherein the tilt axis intersects a definable focal point, which is situated at a definable distance (f) from the rotation device in a z-direction in an initial position of the rotation device, wherein the z-direction extends perpendicularly to the x-direction and perpendicularly to the y-direction; and, a controller configured to displace the connecting rail in the y-direction in relation to the second securing device via the linear actuator when the first securing device is rotated about the tilt axis such that a distance between the focal point and the second securing device is kept constant within a certain interval.

It is a further object to make available a correspondingly advantageous optical apparatus. The aforementioned object can, for example, be achieved by an optical apparatus which includes: an image recording unit; an image rendering unit; a mount having a connecting rail extending in a y-direction; the mount further having a first securing device for the image recording unit and a second securing device for the image rendering unit, wherein the first securing device and the second securing device are mechanically interconnected via the connecting rail; the first securing device and the second securing device being arranged in succession in the y-direction; the connecting rail being arranged so as to be displaceable in the y-direction in relation to the second securing device; the mount having a linear actuator configured to displace the connecting rail in the y-direction in relation to the second securing device; the first securing device including a rotation device;

the rotation device being arranged so as to be rotatable about an axis of rotation extending in an x-direction, wherein the x-direction extends perpendicularly to the y-direction; the rotation device being configured to be rotated about a tilt axis extending in the x-direction by way of a rotation about the axis of rotation and a translation of the connecting rail, wherein the tilt axis intersects a definable focal point, which is situated at a definable distance (f) from the rotation device in a z-direction in an initial position of the rotation device, wherein the z-direction extends perpendicularly to the x-direction and perpendicularly to the y-direction; the mount having a controller configured to displace the connecting rail in the y-direction in relation to the second securing device via the linear actuator when the first securing device is rotated about the tilt axis such that a distance between the focal point and the second securing device is kept constant within a certain interval; and, the image recording unit being secured to the first securing device and the image rendering unit being secured to the second securing device.

It is a further object of the invention to provide a method for operating such an optical apparatus. The aforementioned object can, for example, be achieved by a method for operating an optical apparatus having an image recording unit, an image rendering unit, and a mount having a connecting rail extending in a y-direction; the mount including a first securing device for an image recording unit and a second securing device for an image rendering unit, wherein the first securing device and the second securing device are mechanically interconnected via the connecting rail; the first securing device and the second securing device being arranged in succession in the y-direction; the connecting rail being arranged so as to be displaceable in the y-direction in relation to the second securing device; the mount having a linear actuator configured to displace the connecting rail in the y-direction in relation to the second securing device; the first securing device including a rotation device; the rotation device being arranged so as to be rotatable about an axis of rotation extending in an x-direction, wherein the x-direction extends perpendicularly to the y-direction; the rotation device being configured to be rotated about a tilt axis extending in the x-direction by way of a rotation about the axis of rotation and a translation of the connecting rail, wherein the tilt axis intersects a definable focal point, which is situated at a definable distance from the rotation device in a z-direction in an initial position of the rotation device, wherein the z-direction extends perpendicularly to the x-direction and perpendicularly to the y-direction; the mount having a controller configured to displace the connecting rail in the y-direction in relation to the second securing device via the linear actuator when the first securing device is rotated about the tilt axis such that a distance between the focal point and the second securing device is kept constant within a certain interval; and, the image recording unit being secured to the first securing device and the image rendering unit being secured to the second securing device. The method includes: defining a focal point of the image recording unit and a focal length; defining an initial position of the image rendering unit and of the image recording unit in relation to the connecting rail of the mount and the focal point and determining a distance, emerging therefrom, between the image rendering unit and the focal point; tilting the image recording unit through a defined angle ($\alpha$) about a tilt axis extending through the focal point, wherein the image recording unit is rotated about an axis of rotation extending parallel to the tilt axis via the rotation device; and, moving the connecting rail in a direction extending perpendicularly to the tilt axis in relation to the image rendering unit by one path length (l) on the basis of the focal length and the tilt angle (a) such that the distance between the image rendering unit and the focal point is kept constant within a certain interval.

The mount according to the disclosure is configured for an optical apparatus including an image recording unit and an image rendering unit. The mount includes a first securing device for an image recording unit and a second securing device for an image rendering unit. Here, the first securing device and the second securing device are mechanically interconnected via a connecting rail. The connecting rail extends in a y-direction. The first securing device and the second securing device are arranged in succession in the y-direction. The second securing device is arranged so as to be displaceable along the connecting rail in the y-direction with respect to the first securing device. The mount includes a linear actuator for displacing the connecting rail in the y-direction in relation to the second securing device.

The first securing device includes a rotation device, which is arranged so as to be rotatable about an axis of rotation extending in an x-direction, in particular a mount or a receptacle. Expressed differently, an image recording unit secured to the securing device can be rotated about an axis of rotation extending in the x-direction via the rotation device. The x-direction extends perpendicular to the y-direction. The rotation device is configured to be rotated about a tilt axis extending in the x-direction by way of a rotation about the axis of rotation and by way of a translation or displacement of the connecting rail in the y-direction. The tilt axis intersects a definable focal point, for example the point of intersection of the optical axis with the focal plane. In an initial position of the rotation device, the focal position is situated at a definable distance from the rotation device in a z-direction. The z-direction extends perpendicular to the x-direction and perpendicular to the y-direction.

The mount includes a controller which is configured to displace the connecting rail in the y-direction in relation to the second securing device via the linear actuator when the first securing device is rotated, in particular in conjunction with an image recording unit secured thereto, about the tilt axis such that the distance, for example a certain defined or definable distance, between the focal point and the second securing device is kept constant within a certain interval, for example within a defined or definable interval. By way of example, the distance between the focal point and the second securing device can be kept constant within an interval of ±50 mm, preferably within an interval of ±20 mm, for a rough correction, for example ±10 mm in conjunction with applications within ophthalmology, and of less than ±1 mm for a fine correction. The mount according to the disclosure can be used, in particular, for available surgical microscopes, for example also within the scope of a retrofit. The mount is advantageously configured to be secured to a stand or frame. To this end, the second securing device can include an apparatus for securing the mount to a stand or frame.

Preferably, the controller can be configured to calculate the path by which the connecting rail is displaced in the y-direction on the basis of a focal length and a tilt angle. The focal length is understood to mean the distance between the focal point and the first securing device in the z-direction or, should a specific image recording unit be present, the distance between the focal point and the image recording unit, in particular an objective, along an optical axis of an image recording unit. The tilt angle is understood to mean the angle of rotation of the first securing device or, if present, of the image recording unit about the tilt axis, proceeding from an axis extending in the z-direction. By way of example, the translation path $l$ of the connecting rail can be determined, more particularly calculated, on the basis of the focal length $f$ and the tilt angle $\alpha$, for example.

Preferably, the described change in position on the basis of the tilt angle can be implemented in automated fashion by way of a corresponding linear movement of the first securing device relative to the second securing device, wherein the connecting rail is moved in relation to the second securing device. As a result of the mount according to the disclosure, the absolute movement of the second securing device or of an image rendering unit secured thereon, in particular including further constituent parts of the mount or constituent parts secured thereon, is significantly reduced when the image recording unit is tilted and hence there only still is a minimal influence on the ergonomics of the observer or surgeon, in particular in relation to their distance, viewing angle or observation angle in relation to the image rendering unit.

As a result of the relative movements between the first securing device and the second securing device facilitated by the mount according to the disclosure, displacements of the second securing device resulting from a tilt of the first securing device can be corrected in such a way that the second securing device remains stationary during each tilt but precise tilting can nevertheless be realized. The ergonomics, in particular the observation direction and the observation angle, and the observation distance are not altered for the user. If the tilt is carried out in motor-driven fashion in the case of a surgical microscope, the operator can adapt their observation at any time without interrupting or disturbing the surgical intervention, without a manual correction on the mount or on the stand being required. Dispensing with additional corrective movements on the mount or the stand and the stationary placement of the image rendering unit and of the remaining system resulting therefrom not only improve the ergonomics and reduce the interruptions during an operation but also minimize the risk of a collision.

The mount furthermore is advantageous in that it helps to allow appliances and systems to be constructed as compactly as possible, wherein the disturbance and collision spaces, for example in an operating theatre during the surgery, can be minimized. To this end, the movement spaces for corresponding tilt movements of the first securing device and translation compensation movements of the second securing device are simultaneously minimized.

The specified directions, that is, the x-direction, the y-direction and the z-direction, are any three directions which are perpendicular to one another and which have been denoted by the letters x, y and z. Preferably, the x-direction and the y-direction are directions extending horizontally and the z-direction is a direction extending vertically. Here, the aforementioned directions need not necessarily intersect. Thus, for example, the x-direction and the y-direction could have a distance from one another in the z-direction in a specific application example and would therefore not intersect. However, in this case, there respectively is a direction extending parallel to the specific x-direction, which intersects the specifically selected y-direction of the example.

In an advantageous variant, the first securing device is arranged on the connecting rail so as to be displaceable in the x-direction relative to the second securing device. Here, the mount includes a linear actuator for displacing the first securing device on the connecting rail in the x-direction. The linear actuator can include a position detection device. In this variant, the rotation device can be arranged so as to be rotatable about an axis of rotation extending in the y-direction and can be configured to be rotated about a tilt axis, which extends in the y-direction and intersects the focal point, by way of a rotation of the rotation device about the axis of rotation and a translation or displacement of the connecting rail in the x-direction. Here, the controller is configured to displace the first securing device relative to the second securing device on the connecting rail in the x-direction via the linear actuator when the first securing device is rotated about the tilt axis extending in the y-direction such that the distance between the focal point and the second securing device is kept constant within a certain interval, in particular a defined or definable interval, that is, for example, kept constant within ±5 mm, in particular ±1 mm. This embodiment variant is advantageous in that the first securing device can be tilted in two directions while the position of the second securing device is corrected at the same time.

In a particularly advantageous variant, the first securing device is arranged on the connecting rail so as to be displaceable in the z-direction relative to the second securing device, wherein the mount includes a linear actuator for displacing the first securing device on the connecting rail in the z-direction, and the controller is configured to displace the first securing device relative to the second securing device on the connecting rail in the z-direction via the linear actuator when the first securing device is rotated about the tilt axis extending in the x-direction or y-direction such that the distance between the focal point and the second securing device is kept constant within a certain interval.

The aforementioned translation movements of the first and/or second securing device and/or of the connecting rail can be undertaken automatically by the specified linear actuators, in particular in a controlled fashion by way of the control device. A displaceability of the connecting rail and/or of the first and/or second securing device in one or more of the aforementioned directions is advantageous in that the first securing device and, in particular, an image recording unit secured thereon can be rotated precisely about one or more tilt axes. As a result of the displaceability in a plurality of directions, it is possible to keep the focal length constant or precisely correct the latter when necessary. Moreover, the aforementioned linear actuators facilitate an automatic translation, in particular a translation controlled by way of a controller, of the connecting rail and/or of the first and/or second securing device in one or more of the aforementioned directions.

By way of example, the mount can be configured for distances between the focal point and the first securing device of between 100 mm and 300 mm, preferably of between 150 mm and 250 mm. In addition or as an alternative thereto, the mount can be configured for tilt angles about one or more tilt axes of between −20 degrees and +50 degrees, for example between −15 degrees and +45 degrees, depending on the desired application also between −10 degrees and +30 degrees, proceeding from the initial position of the first securing device. The aforementioned tilt angle ranges are advantageous in that they are particularly suitable for an application for optical apparatuses in the medical field.

The mount can furthermore be configured for a displaceability of the connecting rail in relation to the second securing device of no more than 300 mm in the y-direction. A corresponding displaceability in the x-direction is likewise possible. However, a displaceability of no more than 100 mm, that is, ±50 mm (respectively 50 mm to the right or left from the central position), in the x-direction is advantageous in order, in particular, to ensure the stability of the mount.

The optical apparatus according to the disclosure includes an image recording unit and an image rendering unit. Moreover, it includes an above-described mount, when the image recording unit is secured to the first securing device and the image rendering unit is secured to the second securing device. The optical apparatus has the features and advantages already specified above in conjunction with the mount according to the disclosure. By way of example, the optical apparatus according to the disclosure can be a surgical microscope. Here, the surgical microscope is an ophthalmic surgical microscope and/or a surgical microscope for neurosurgery and/or a surgical microscope for dentistry and/or a microsurgical surgical microscope. The image recording unit can include a digiscope. The image rendering unit can include a monitor and/or a digital eyepiece.

The method for operating an optical apparatus as described above includes the following steps: A focal point, for example any point in a focal plane, of the image recording unit and a focal length are defined. An initial position of the image rendering unit and of the image recording unit in relation to the connecting rail of the mount and the focal point are defined, for example by virtue of the coordinates of the focal point and/or of the image rendering unit and/or of the image recording unit and/or of the connecting rail being determined, in particular calculated, in a Cartesian coordinate system. Furthermore, a distance between the image rendering unit and the focal point, which arises from the initial position and the focal point, is defined, in particular calculated from the coordinates.

The image recording unit is rotated by a defined angle about a tilt axis extending through the focal point, that is, expressed differently, tilted. Here, the image recording unit is rotated via the rotation device about an axis of rotation extending parallel to the tilt axis. The connecting rail is moved, in particular displaced, in a direction extending perpendicular to the tilt axis in relation to the image rendering unit by one path length on the basis of the focal length and the tilt angle such that the distance between the image rendering unit and the focal point is kept constant within a certain interval. The interval may be defined or may have been defined. By way of example, the interval can be no more than ±5 mm, in particular no more than ±1 mm or else 0 mm. In the latter case, the distance is kept precisely constant.

In an advantageous variant, the focal length is between 100 mm and 300 mm, in particular between 150 mm and 250 mm. In addition or as an alternative thereto, the tilt angle can lie between −20 degrees and +50 degrees, for example between −15 degrees and +45 degrees or, depending on the requirements of the application, in a smaller angle range. The path length can be between 0 mm and 300 mm, or else be less.

The connecting rail can be displaced by a path length l which, should the tilt axis coincide with the optical axis, is proportional to the distance x between the focal point and the axis of rotation and the tangent of the tilt angle α, that is, which is determined according to $$l \sim x^* \tan \alpha$$

in particular calculated according to $$l = x^* \tan \alpha$$

The specified path length can be a translation length of the connecting rail in the y-direction.

The method according to the disclosure has the advantages already specified above. It facilitates, particularly in conjunction with medical applications, particularly in conjunction with surgical microscopes, an improvement of the ergonomic comfort of a user, in particular a surgeon, and moreover offers improved handling with, at the same time, an increased precision of the tilt of an image recording unit while correcting the position of the image rendering unit at the same time.

Overall, embodiments of the present disclosure are particularly suitable for applications in eye surgery or ophthalmic microsurgery but are otherwise also suitable for any application which requires a precise tilt of an image capturing device with a simultaneous correction of a position of an image rendering unit that was altered by the tilt movement.

The invention is explained in greater detail below on the basis of exemplary embodiments and with reference to the accompanying figures. Although the invention is more specifically illustrated and described in detail by means of the preferred embodiments, nevertheless the invention is not restricted by the examples disclosed and other variations can be derived therefrom by the person skilled in the art, without departing from the scope of protection of the invention.

The figures are not necessarily accurate in every detail and to scale and can be presented in enlarged or reduced form for the purpose of better clarity. For this reason, functional details disclosed here should not be understood to be limiting, but merely to be an illustrative basis that gives guidance to a person skilled in this technical field for using the present invention in various ways.

The expression "and/or" used here, when it is used in a series of two or more elements, means that any of the elements listed can be used alone, or any combination of two or more of the elements listed can be used. For example, if a structure is described as containing the components A, B and/or C, the structure can contain A alone; B alone; C alone; A and B in combination; A and C in combination; B and C in combination; or A, B, and C in combination.

BRIEF DESCRIPTION OF THE DRAWINGS

The invention will now be described with reference to the drawings wherein.

DESCRIPTION OF THE PREFERRED EMBODIMENTS OF THE INVENTION

Figure 1:
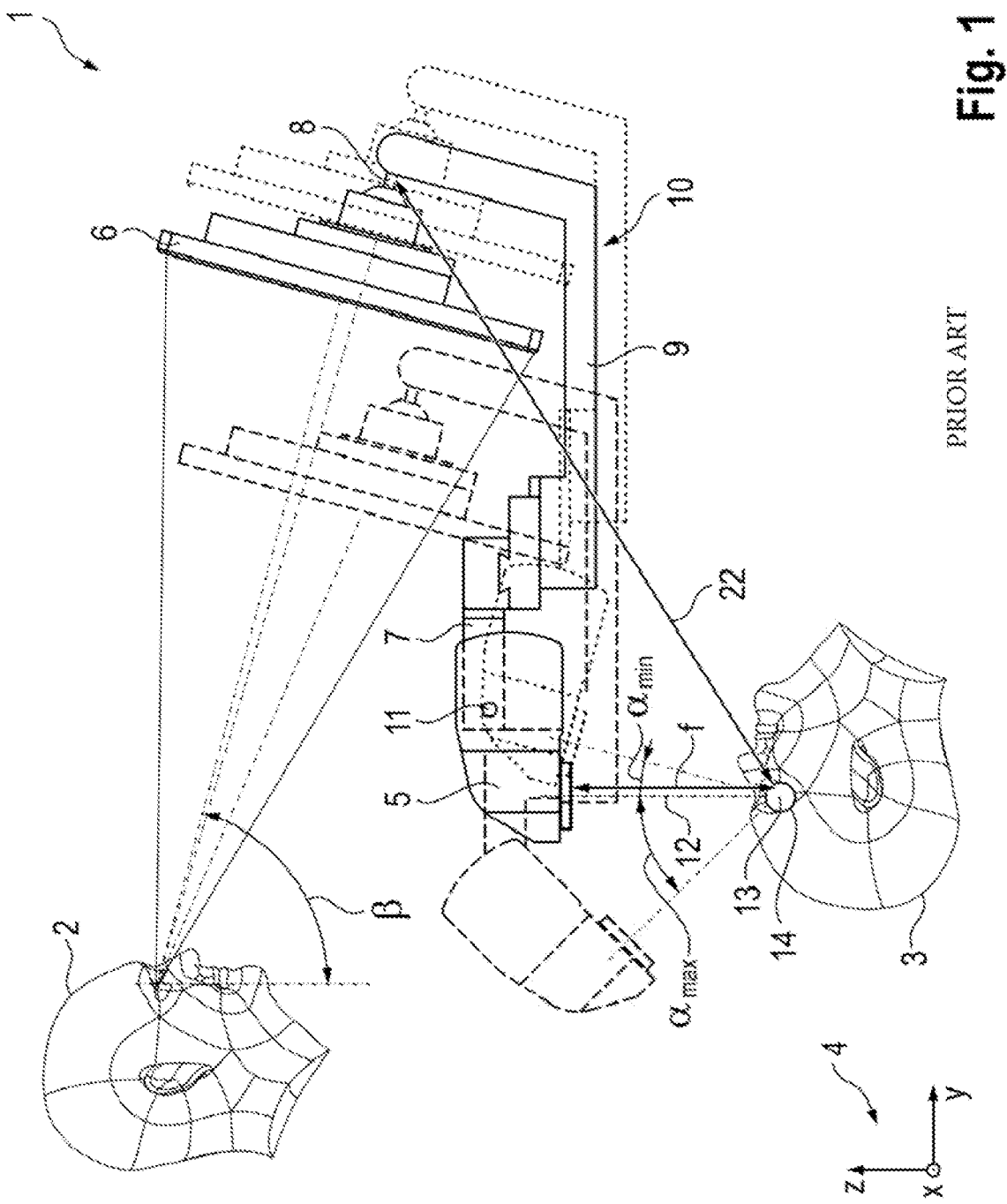
FIG. 1 schematically shows the basic structure and the arrangement of a digital surgical microscope in a microsurgical intervention in ophthalmology.

FIG. 1 schematically shows the basic structure and the arrangement of a digital surgical microscope in a microsurgical intervention in ophthalmology. Here, the shown digital surgical microscope 1 is used by a surgeon 2 for carrying out an eye operation on a patient 3. Here, a first, a second and a third spatial direction are labeled by a coordinate system 4. Here, the z-direction denotes the vertical direction and the x-direction and the y-direction denote horizontal directions. Here, the x-direction, the y-direction and the z-direction are each perpendicular to one another.

The digital surgical microscope 1 includes an image recording unit 5, an image rendering unit 6 and a mount 10. In the variant shown, the image recording unit 5 is embodied as a digiscope and the image rendering unit is embodied as a monitor. The mount 10 includes a connecting rail 9. A first securing device 7, to which the image recording unit 5, the digiscope in the present case, is secured, and a second securing device 8, to which the image rendering unit 6, for example the monitor, is secured, are arranged on the connecting rail 9, which extends in the y-direction in the variant shown. Moreover, the first securing device 7 includes a rotation device with an axis of rotation 11 extending in the x-direction, the rotation device being configured to rotate the digiscope 5 secured thereto about the axis of rotation 11.

The digiscope 5 has an optical axis 12. The digiscope is focused on a focal point 13 during the operation. The latter is situated in spaced apart fashion at a defined distance, usually the focal length f, from the digiscope 5 along the optical axis 12. The distance between the focal point 13 and the second securing device 8, which arises from the defined focal point 13 and the initial position of the surgical microscope 1, is labeled by the reference line 22.

During operation, it may be necessary to tilt the digiscope 5 within a defined angular range Δα about a tilt axis 14 extending in the x-direction and extending through the focal point 13. In FIG. 1, the absolute positions of the individual components of the surgical microscope are labeled schematically by dotted lines for different tilt angles α. In the shown variant, a tilt through a minimum tilt angle $α_{min}$ of −15 degrees and a maximum tilt angle $α_{max}$ of +45 degrees is possible here, proceeding from a vertically arranged optical axis 12, that is, proceeding from the z-direction.

To realize focusing on the focal point 13 while maintaining the focal length f, the digiscope 5 is rotated about the axis of rotation 11 and the mount 10 is displaced or moved in translation over a relatively large distance in the y-direction and over a relatively small distance in the z-direction during this tilt. As a result of moving the mount 10, there is, at the same time, a change in the absolute position of the monitor 6 and hence also change in the distance 22 between the focal point 13 and the second securing device 8. Moreover, there is, firstly, a change in the observation angle β of the observer or surgeon 2 and in the observation distance, that is, the distance between the observer 2 and monitor 6. As already explained in the introductory part of the description, such a change in the observation angle and/or observation distance is undesirable since 3D monitors, in particular, generally require a defined observation angle and observation distance for a correct perception of the 3D image representation. The compensation/correction movement in the y- and z-direction is usually implemented by hand by way of alterations on the frame/stand in this case. Such approximate positioning leads to an interruption of the operation and might be carried out in non-sterile fashion under certain circumstances. In addition to the ergonomic restrictions, the manual compensation/correction movement is a significant disadvantage of this embodiment.

In general, a tilt of the digiscope 5 leads, in particular, to a significant change in position of the arrangement perpendicular to the tilt axis 14, for example in the y-direction. To reduce the displacement of the image rendering unit 6 with respect to the observer, in particular the surgeon 2, which emerges from the tilt, this change in position is at least partly compensated in automated fashion and on the basis of the tilt angle within the scope of the present disclosure by way of an additional linear movement of the image recording device 5 in the y-direction relative to the image rendering device 6. To this end, a separate linear actuator 15 is provided, or else the travel of an available linear unit of the xy-coupling is extended accordingly. Hence, the absolute movements of the image rendering unit 6 are significantly reduced when the image recording unit 5 is tilted and the ergonomics of the observer 2, in particular the observation distance and the view and the observation angle, are only still influenced to a minimal extent.

However, a correction of the stand position in the z-direction in the case of a tilt may still be necessary under certain circumstances, even if only to a significantly smaller extent. As a result of a further relative movement of the image recording unit 5 with respect to the image rendering unit 6 in the z-direction, the displacement resulting from the tilt can be corrected in such a way that the image rendering unit 6 remains stationary during every tilt. Ergonomics and observation are therefore not altered for the surgeon 2. If the tilt is carried out in motor-driven fashion, the operator 2 can adapt their observation, that is, for example, the observation direction and the image section, at any time without interrupting or disturbing the surgical intervention, in particular without needing corrections or movements or alterations on the mount 10 or a stand. Dispensing with additional corrective movements on the mount 10 and the stationary placement of the image rendering unit 6 and of the remaining system not only improve the ergonomics and reduce the interruptions during an operation but also minimize the risk of aforementioned collisions.

Figure 2:
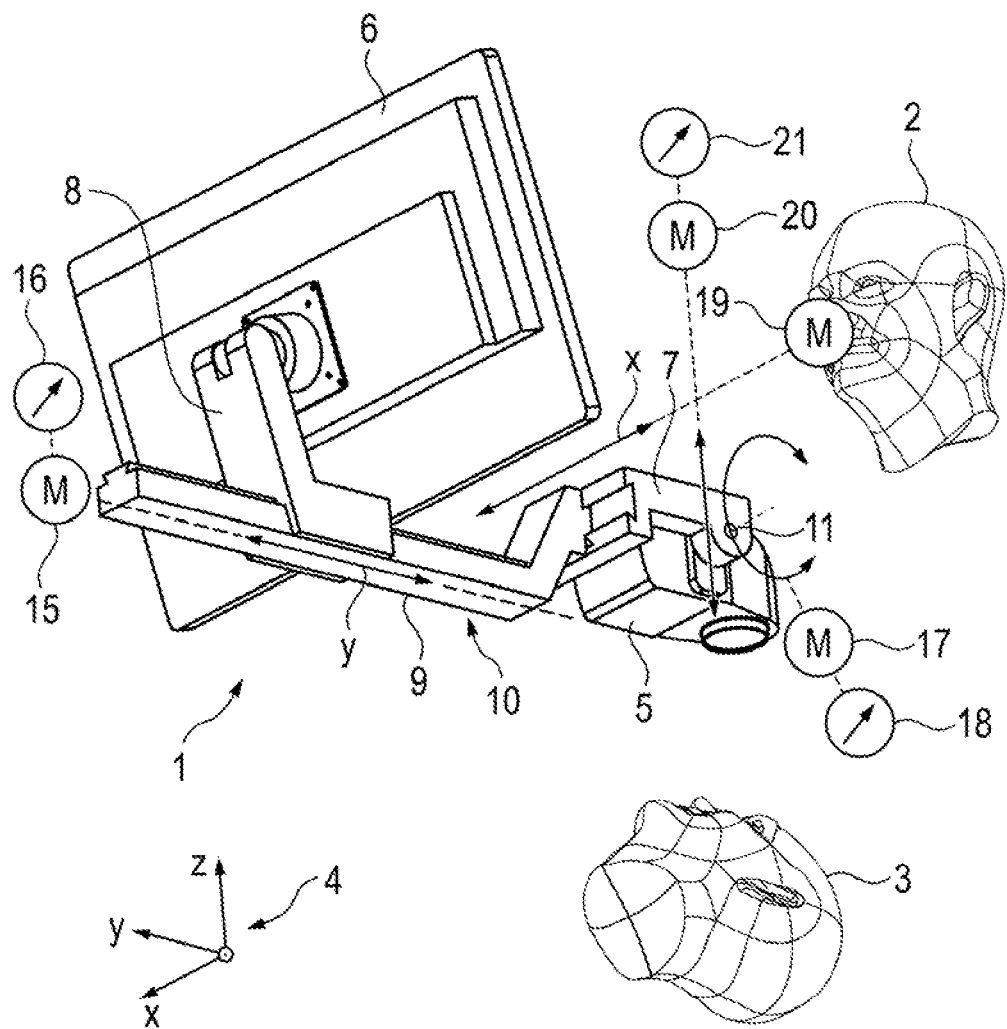
FIG. 2 schematically shows a variant of a surgical microscope according to the disclosure in a perspective view.

FIG. 2 schematically shows a variant of a surgical microscope in a perspective view. Deviating from the embodiment shown in FIG. 1, it is possible to manipulate the relative distance between the first securing device 7 and the second securing device 8 by displacing the connecting rail 9 in the y-direction.

Preferably, the second securing device is secured to a frame, which is placed in the room in stationary fashion. To carry out a corresponding displacement, provision is made of a linear actuator 15 and a position detection device 16, wherein fine positioning can also be implemented herewith. Furthermore, provision is made of an actuator 17 and a position detection device 18 for carrying out a rotation of the digiscope 5 about the axis of rotation 11. Optionally, provision can also be made of a further linear actuator 19, possibly with a position detection device, for the displacement or translational movement of the digiscope 5 in the x-direction for fine positioning purposes. To correct the focal length f or for focusing purposes, provision can be made of a linear actuator 20 and a position detection device 21 within the scope of the rotation apparatus, which facilitates a displacement of the digiscope 5 in the direction of the optical axis.

Figure 3:
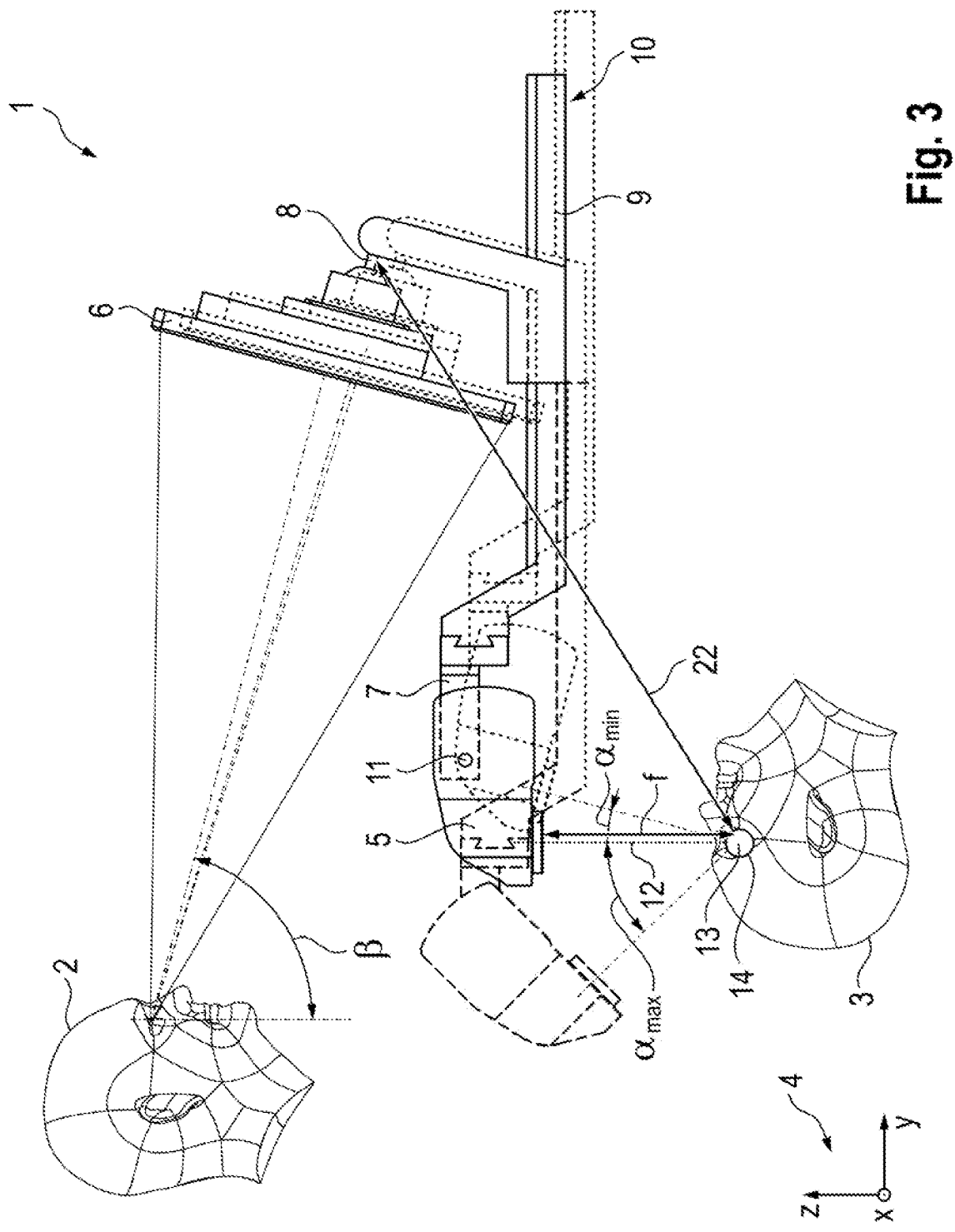
FIG. 3 schematically shows a side view of the variant shown in FIG. 2.

A side view of this embodiment variant is shown schematically in FIG. 3. The initial position of the surgical microscope 1 is labeled using a solid line and the respective absolute positions for different tilt angles α are labeled by dotted lines. Here, the displacement of the first securing device 7 and of the image recording unit 5 relative to the second securing device 8 and the monitor 6 in the y-direction is implemented in such a way that a distance between the focal point 13 and the second securing device 8 or the monitor 6, defined for an initial position, is preferably kept constant or is at least kept constant within a defined error interval or within a defined distance interval. The distance between the focal point 13 and the second securing device 8 for the initial position is denoted by the reference sign 22 in the figures. While the distance 22 varies quite significantly for different tilt angles α in the embodiment shown in FIG. 1, it is virtually constant in the variant according to the invention shown in FIG. 3. Further embodiment variants, in which the distance 22 between the focal point 13 and the second securing device 8 can be kept constant in an even more precise manner, are described in the following embodiment variants.

In order to construct appliances and systems as compact as possible, in particular in order to minimize disturbance and collision spaces in an operating theater and during an operation, it is advantageous to restrict the movement of spaces for linear and tilt movements. On the basis of the requirements of the user, in particular the adjustment range of an xy-coupling, the focal length and the focusing range, and the tilt range, it is possible in the case of an appropriate appliance-technical arrangement to appropriately select and define the travels for all linear actuators.

In principle, the controller is provided to control the mount 10, that is, specifically the position of the first securing device 7 and the second securing device 8 in relation to the connecting rail 9, the controller being configured to displace the connecting rail 9, and hence the second securing device 8 along the connecting rail 9 in relation to the first securing device 7, in the y-direction in such a way when the first securing device 7 is rotated about the tilt axis 14, that is, expressed differently, in the case of a rotation of the rotation device about the axis of rotation 11, that a defined distance 22 between the focal point 13 and the second securing device 8 is maintained within a defined interval. By way of example, the defined distance 22 can be defined for an initial position, which might be, for example, a setting at the start of an operation.

The sought-after error interval can be adapted, for example, to the requirements of the respective measure to be carried out and to the needs of the user. By way of example, an error interval of ±5 mm or ±1 mm might be considered sufficient. However, a smaller interval might also be desirable for specific applications; this can be realized via embodiments of the present disclosure.

In a manner analogous to the described correction for the position of the first securing device 7 and the image recording unit 5 relative to the second securing device 8 and the monitor 6 in the y-direction, there can be a correction of the position of the first securing device 7 and the image recording unit 5 relative to the second securing device 8 and the monitor 6 in the x-direction in the case of a tilt of the first securing device 7 and of the digiscope 5 about a tilt axis extending in the y-direction. For this variant, the rotation device of the first securing device 7 can include an axis of rotation extending in the y-direction, which facilitates a twist of the digiscope 5 about this axis. Furthermore, for the purpose of realizing a tilt about a tilt axis which extends in the y-direction and which extends through the focal point 13, the first securing device 7 and/or the connecting rail 9 can be configured to be displaceable in the x-direction during such a tilt. To correct the position of the first securing device 7 and the image recording unit 5, the first securing device 7 can be arranged to be displaceable relative to the second securing device 8, in this case on the connecting rail 9 in the x-direction.

Figure 4:
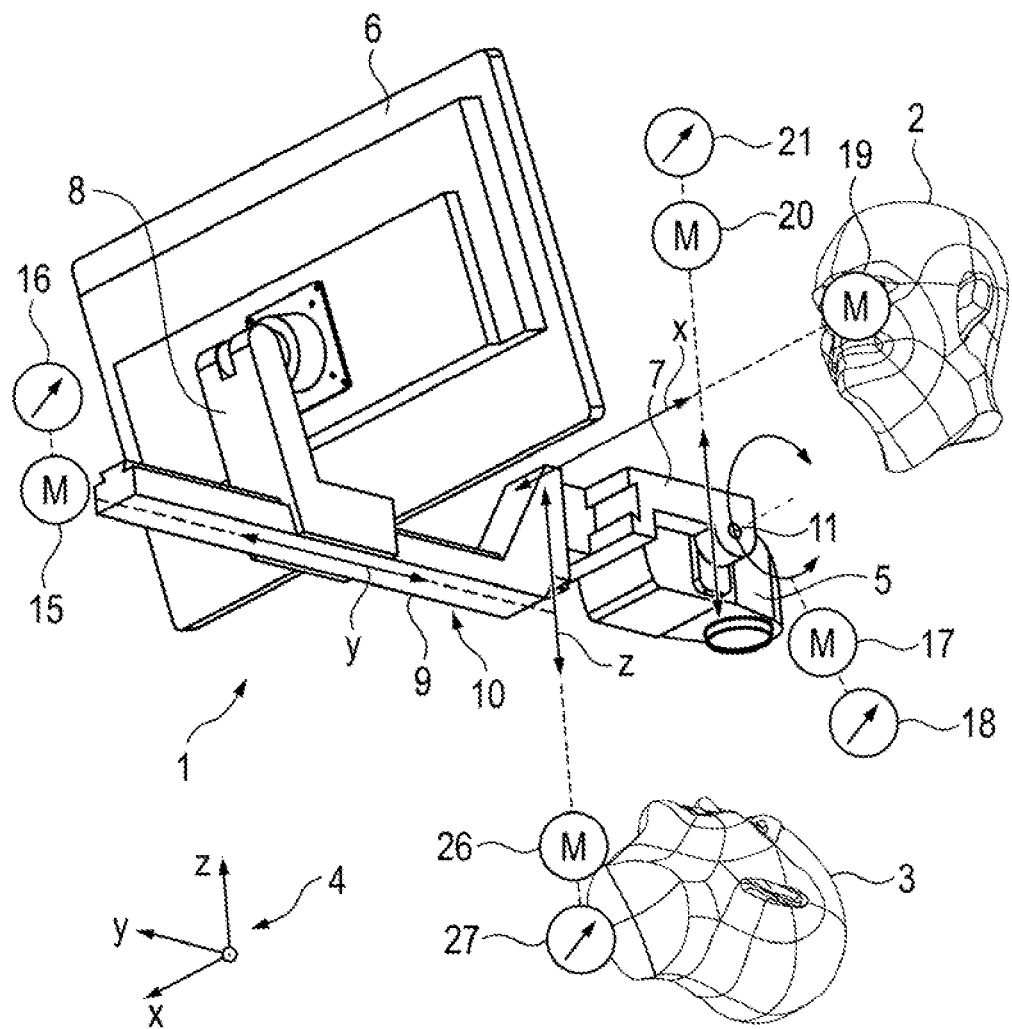
FIG. 4 schematically shows a further variant of a surgical microscope in a perspective view.
Figure 5:
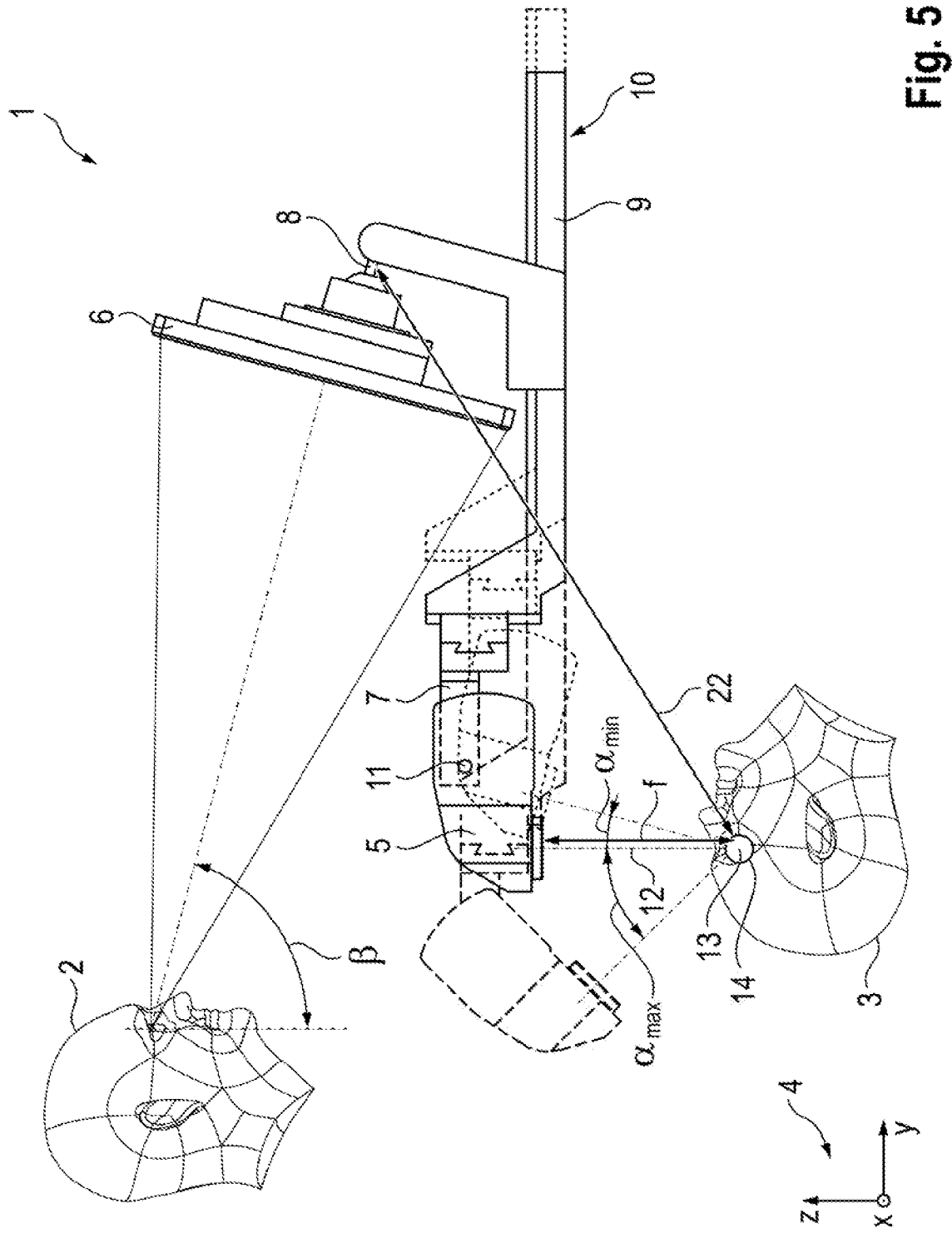
FIG. 5 schematically shows a side view of the variant shown in FIG. 4.

FIGS. 4 and 5 show an embodiment variant which additionally facilitates a translation of the first securing device 7 in the z-direction. To this end, provision can be made of a further linear actuator 26 with a position detection device 27. Using this embodiment variant, it is possible to very precisely keep the distance 22 between the focal point 13 and the second securing device 8 and/or monitor 6 constant. As a result, the observation angle β and the observation distance of the user, in particular the surgeon 2, from the monitor 6, that is, ultimately, the absolute position of the monitor 6, is thus kept constant very precisely, despite the tilt of the digiscope 5.

Figure 6:
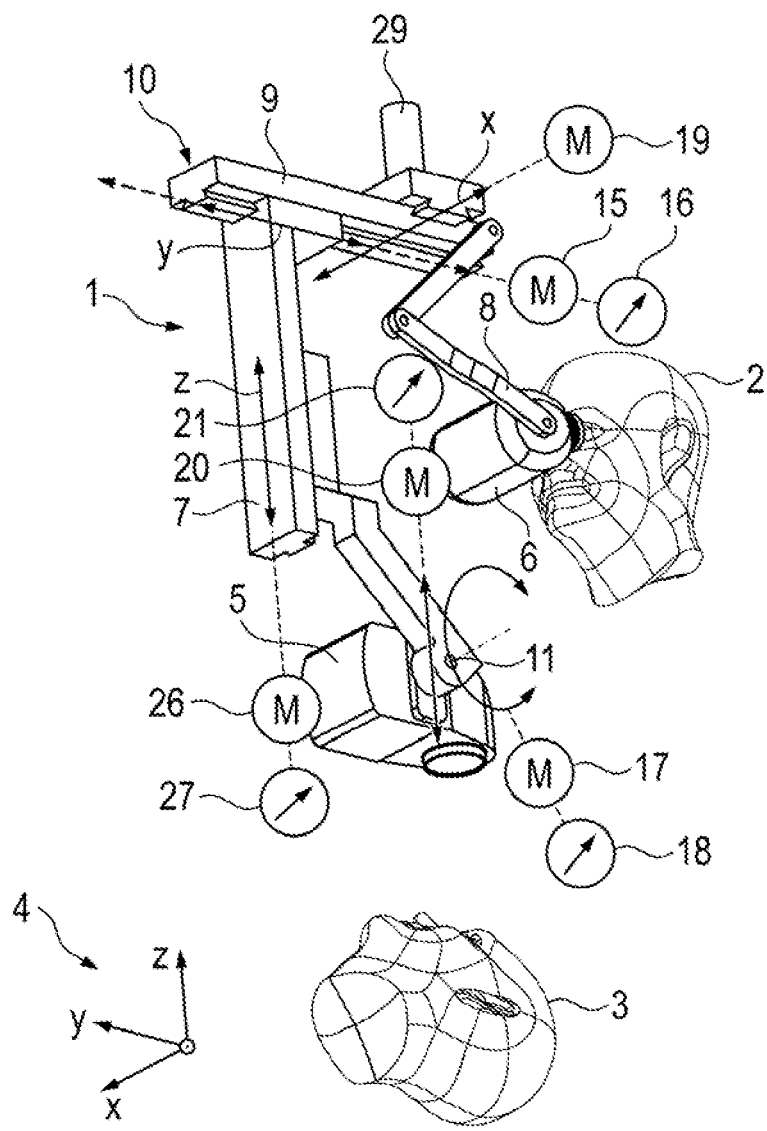
FIG. 6 schematically shows another variant of a surgical microscope in a perspective view.
Figure 7:
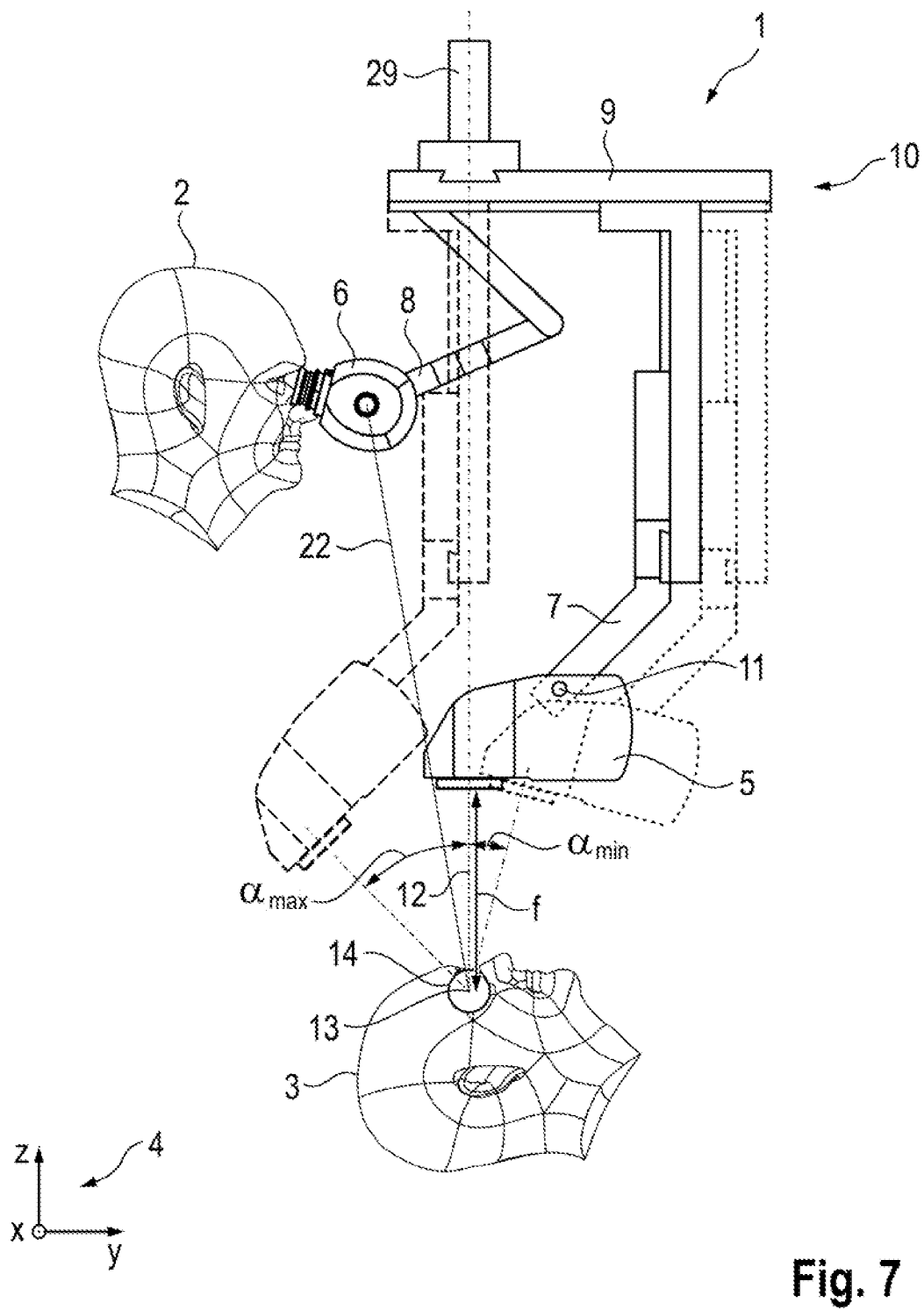
FIG. 7 schematically shows a side view of the variant shown in FIG. 6.

FIGS. 6 and 7 show a further embodiment, in which a digital eyepiece is used as an image rendering unit 6 in place of the monitor. Furthermore, in the variant shown, the mount 10 includes a vertical securing device 29, as a result of which it can be mounted on a stand or frame, for example. Advantageously, the vertical securing device 29 is arranged in such a way that, as shown in FIG. 7, it includes a central axis which extends along the optical axis 12 of the image recording unit 5, for example the digiscope, for tilt angles of 0 degrees. As a result, there can be a simultaneous rotation of the digiscope 5 about the optical axis 12 by way of a rotation of the surgical microscope 1 about the central axis of the mount 29. Thus, for example, if a rotation about the central axis is detected, decentration caused thereby can also be compensated by way of an xy-coupling arranged on the mount 29 such that there always is a rotation about the image center, even in the case of a rotation about an axis of rotation extending in the z-direction, and hence no corrections by way of the mount 10 become necessary. Otherwise, all features and embodiments specified in conjunction with the above-described embodiments and variants can be realized for a digital eyepiece, in a manner analogous to an arrangement with the monitor.

Figure 8:
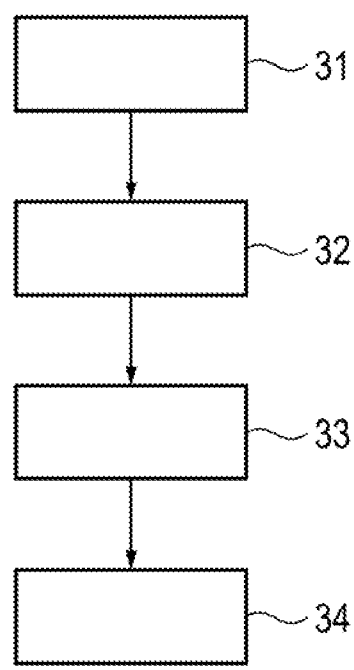
FIG. 8 schematically shows a method according to the disclosure in the form of a flowchart.

A possible application of a surgical microscope 1 according to the invention is described below. FIG. 8 schematically shows a method according to the invention in the form of a flowchart. The focal point 13 of the image recording unit 5 and the focal length f are defined in a first step 31. To this end, the available linear units are aligned with a defined initial or central position and the image recording unit 5 is aligned in vertical fashion, that is, with a tilt angle ? of 0 degrees, for example before the initial setup and placement of the surgical microscope 1 according to the invention over the patient 3. In this case, brought into an initial position are a linear unit in the x-direction for manipulating the image center and a linear unit in the y-direction for manipulating the image center and optionally with an extended adjustment range for compensation movement in the case of a tilt. Where necessary, brought into an initial position is an additional linear unit in the y-direction for the compensation movement in the case of a tilt. Brought into an initial position are a linear unit for focusing, that is, for manipulating the focal plane, and a linear unit in the z-direction for a compensation movement in the case of a tilt.

If a focus drive 20 with an absolute position detection 21, a drive 17 for a tilt with an absolute position detection 18, a linear drive 15 for a y-compensation movement with an absolute position detection 16 and a linear drive 26 for a z-compensation movement with an absolute position detection 27 are present, this step could also be skipped and, depending on the selected position of the tilt (position detection 18) and the focal position (position detection 21), a corresponding position for a y-compensation (drive 15) and a z-compensation (drive 26) could be calculated and, for example, stored and subsequently be set or approached.

In the next step 32, an initial position of the image rendering unit 5 is defined in relation to the connecting rail 9 and the focal point 13 and a distance, arising therefrom, is determined between the image recording unit 5 and the focal point 13. The image recording unit 5 and the image rendering unit 6 are placed, for example over the patient 3, using the mount 10. To this end, the object center and object plane are initially roughly aligned and subsequently the image recording unit 5 is finely positioned via the xy-coupling for the object center and the focus for the object plane. The image rendering unit 6, for example the monitor or the digital eyepiece, is configured in respect of the observer 2, in a manner adapted to the requirements thereof.

Subsequently, the surgical intervention can be started, wherein all changes in position of the image recording unit 5 by the surgeon 2 can be initiated under sterile conditions, for example in motor-driven fashion by way of a foot switch, without the surgeon having to interrupt their work for the purposes of correction movements on the stand or the mount-like. In step 33, the image recording unit 5 is tilted through a defined angle α about a tilt axis 14 extending through the focal point 13, wherein the image recording unit 5 is rotated about an axis of rotation 11 extending parallel to the tilt axis 14 via the rotation device.

Subsequently or simultaneously, the connecting rail 9 is displaced in step 34 in a direction extending perpendicular to the tilt axis 14 in relation to the image rendering unit 6 by one path length I on the basis of the focal length f and the tilt angle α such that the distance 22 between the image rendering unit 6 and the focal point 13 is kept constant within a certain interval. Specifically, the image recording unit 5 is for example tracked automatically relative to the image rendering unit 6 by way of the compensation movements, in particular compensation movements in the z- and y-direction, in a manner dependent on the tilt. Optionally, a tilt about a tilt axis parallel to the y-direction can additionally be undertaken, wherein a corresponding compensation movement can be implemented in the z- and x-direction.

Should the linear actuator 26 have correspondingly large dimensions for a z-compensation movement, that is, the travel, the latter can also realize the vertical position of the image recording unit 5, in particular of the digiscope, and hence also the focusing movement in the case of a tilt angle of 0 degrees. Consequently, the linear actuator 20 only still needs to carry out a relatively small correction movement in the case of a tilt. The focus, which is situated in the compact digiscope 5, could consequently have an even more compact embodiment without the overall focusing range being limited too strongly. Furthermore, fast lifting and lowering of the microscope 1 could be realized by way of the linear actuator 26 with an extended travel for the z-compensation movement.

It is understood that the foregoing description is that of the preferred embodiments of the invention and that various changes and modifications may be made thereto without departing from the spirit and scope of the invention as defined in the appended claims.

LIST OF REFERENCE SIGNS

1 Digital surgical microscope
2 Surgeon
3 Patient
4 Coordinate system
5 Image recording unit
6 Image rendering unit
7 First securing device
8 Second securing device
9 Connecting rail
10 Mount
11 Axis of rotation
12 Optical axis
13 Focal point
14 Tilt axis
15 Linear actuator
16 Position detection device 17 Actuator
18 Position detection device
19 Linear actuator, optionally with a position detection device
20 Linear actuator
21 Position detection device
22 Distance
26 Linear actuator
27 Position detection device
29 Vertical securing device
31 Defining a focal point of the image recording unit and a focal length
32 Defining an initial position of the image rendering unit and of the the image recording unit in relation to the connecting rail of the mount and the focal point and determining a distance, emerging therefrom, between the image rendering unit and the focal point
33 Tilting the image recording unit through a defined angle about a tilt axis extending through the focal point, wherein the image recording unit is rotated about an axis of rotation extending parallel to the tilt axis via the rotation device,
34 Moving the connecting rail in relation to the image rendering unit in a direction extending perpendicular to the tilt axis by one path length on the basis of the focal length and the tilt angle such that the distance between the image rendering unit and the focal point is kept constant within a certain interval.
f Focal length
$\alpha$ Tilt angle
$\alpha_{min}$ Minimum tilt angle
$\alpha_{max}$ Maximum tilt angle
$\beta$ Observation angle

What is claimed is:

1. A mount for an optical apparatus having an image recording unit and an image rendering unit, the mount comprising:
    a connecting rail extending in a y-direction;
    a first securing device for accommodating said image recording unit thereon and a second securing device for accommodating said image rendering unit thereon, wherein said first securing device and said second securing device are mechanically interconnected via said connecting rail;
    said first securing device and said second securing device being arranged in succession in the y-direction;
    said connecting rail being arranged so as to be displaceable in the y-direction in relation to said second securing device;
    a linear actuator configured to displace said connecting rail in the y-direction relative to said second securing device;
    said first securing device including a rotation device mounted thereon;
    said rotation device defining a rotational axis extending in an x-direction and being configured to rotate said image recording unit about said rotational axis;
    said x-direction extending perpendicularly to said y-direction;
    said image recording unit with said rotation device being rotatable about a tilt axis extending in said x-direction via a combined movement of said image recording unit with said rotation device about said rotational axis and a translational movement of said connecting rail in said y-direction;
    wherein the tilt axis intersects a definable focal point, which is situated at a definable distance (f) from said rotation device in a z-direction in an initial position of said rotation device, wherein the z-direction extends perpendicularly to the x-direction and perpendicularly to the y-direction; and,
    a controller configured to displace said connecting rail in the y-direction relative to said second securing device via said linear actuator when said image recording unit with said rotation device is rotated about said rotational axis to effect said combined movement about the tilt axis such that a distance between the focal point and said second securing device is kept constant within a predetermined interval.

2. A mount for an optical apparatus having an image recording unit and an image rendering unit, the mount comprising:
    a connecting rail extending in a y-direction;
    a first securing device for accommodating said image recording unit thereon and a second securing device for accommodating said image rendering unit thereon, wherein said first securing device and said second securing device are mechanically interconnected via said connecting rail;
    said first securing device and said second securing device being arranged in succession in the y-direction;
    said connecting rail being arranged so as to be displaceable in the y-direction relative to said second securing device;
    a first linear actuator configured to displace said connecting rail in the y-direction relative to said second securing device;
    said first securing device including a rotation device mounted thereon;
    said rotation device defining a rotational axis extending in the y-direction and being configured to rotate said image recording unit about said rotational axis;
    said y-direction extending perpendicularly to an x-direction;
    said image recording unit with said rotation device being rotatable about a tilt axis extending in said y-direction via a combined movement of said image recording unit with said rotation device about said rotational axis and a translational movement of said connecting rail in said x-direction;
    said first securing device being arranged on said connecting rail so as to be displaceable in the x-direction relative to said second securing device;
    wherein the mount further comprises a second linear actuator configured to displace said first securing device on said connecting rail in the x-direction;
    wherein the tilt axis intersects a definable focal point, which is situated at a definable distance (f) from said rotation device in a z-direction in an initial position of said rotation device, wherein the z-direction extends perpendicularly to the x-direction and perpendicularly to the y-direction; and,
    a controller configured to displace said first securing device relative to said second securing device on said connecting rail in said x-direction via said second linear actuator when said image recording unit with said rotation device is rotated about said rotational axis to effect said combined movement about the tilt axis such that a distance between the focal point and said second securing device is kept constant within a predetermined interval.

3. The mount of claim 2, wherein
    said first securing device is arranged on said connecting rail so as to be displaceable in the z-direction relative to said second securing device, wherein the mount further comprises a third linear actuator for displacing said first securing device on said connecting rail in the z-direction; and, said controller is configured to displace said first securing device relative to said second securing device on said connecting rail in the z-direction via said third linear actuator when said rotation device of said first securing device is rotated about the tilt axis extending in the x-direction or a second tilt axis in the y-direction such that the distance between the focal point and the second securing device is kept constant within a certain interval.

4. The mount of claim 1, wherein said linear actuator is a first linear actuator; said first securing device is arranged on said connecting rail so as to be displaceable in the z-direction relative to said second securing device; wherein the mount further comprises a second linear actuator for displacing said first securing device on said connecting rail in the z-direction; and, said controller is configured to displace said first securing device relative to said second securing device on said connecting rail in the z-direction via said second linear actuator when said first securing device is rotated about the tilt axis extending in the x-direction or a tilt axis in the y-direction such that the distance between the focal point and the second securing device is kept constant within a certain interval.

5. The mount of claim 1, wherein the mount is configured for distances between the focal point and the first securing device of between 100 mm and 300 mm and tilt angles between −20 degrees and +50 degrees proceeding from an initial position of said first securing device and/or a displaceability of said connecting rail of 300 mm in the y-direction.

6. The mount of claim 1, wherein the second securing device includes a structure for securing the mount to a stand.

7. An optical apparatus comprising:
an image recording unit;
an image rendering unit;
a mount having a connecting rail extending in a y-direction,
a mount including:
a connecting rail extending in a y-direction;
a first securing device for accommodating said image recording unit thereon and a second securing device for accommodating said image rendering unit thereon, wherein said first securing device and said second securing device are mechanically interconnected via said connecting rail;
said first securing device and said second securing device being arranged in succession in the y-direction;
said connecting rail being arranged so as to be displaceable in the y-direction in relation to said second securing device;
a linear actuator configured to displace said connecting rail in the y-direction relative to said second securing device;
said first securing device including a rotation device mounted thereon;
said rotation device defining a rotational axis extending in an x-direction and being configured to rotate said image recording unit about said rotational axis;
said x-direction extending perpendicularly to said y-direction;

said image recording unit with said rotation device being rotatable about a tilt axis extending in said x-direction via a combined movement of said image recording unit with said rotation device about said rotational axis and a translational movement of said connecting rail in said v-direction;

wherein the tilt axis intersects a definable focal point, which is situated at a definable distance (f) from said rotation device in a z-direction in an initial position of said rotation device, wherein the z-direction extends perpendicularly to the x-direction and perpendicularly to the y-direction; and, a controller configured to displace said connecting rail in the y-direction relative to said second securing device via said linear actuator when said image recording unit with said rotation device is rotated about said rotational axis to effect said combined movement about the tilt axis such that a distance between the focal point and said second securing device is kept constant within a predetermined interval.

8. The optical apparatus of claim 7, wherein the optical apparatus is a surgical microscope.

9. The optical apparatus of claim 8, wherein the surgical microscope is at least one of an ophthalmic surgical microscope, a surgical microscope for neurosurgery, and a surgical microscope for dentistry.

10. The optical apparatus of claim 7, wherein said image recording unit includes a digiscope.

11. The optical apparatus of claim 7, wherein said image rendering unit includes at least one of a monitor and a digital eyepiece.

12. A method for operating an optical apparatus having an image recording unit, an image rendering unit, and a mount having a connecting rail extending in a y-direction; image recording unit and a second securing device for an image a first securing device for accommodating said image recording unit thereon and a second securing device for accommodating said image rendering unit thereon, wherein said first securing device and said second securing device are mechanically interconnected via said connecting rail; said first securing device and said second securing device being arranged in succession in the y-direction; said connecting rail being arranged so as to be displaceable in the y-direction in relation to said second securing device; a linear actuator configured to displace said connecting rail in the y-direction relative to said second securing device; said first securing device including a rotation device mounted thereon; said rotation device defining a rotational axis extending in an x-direction and being configured to rotate said image recording unit about said rotational axis; said x-direction extending perpendicularly to said y-direction; said image recording unit with said rotation device being rotatable about a tilt axis extending in said x-direction via a combined movement of said image recording unit with said rotation device about said rotational axis and a translational movement of said connecting rail in said y-direction; wherein the tilt axis intersects a definable focal point, which is situated at a definable distance (f) from said rotation device in a z-direction in an initial position of said rotation device, wherein the z-direction extends perpendicularly to the x-direction and perpendicularly to the y-direction; and, a controller configured to displace said connecting rail in the y-direction relative to said second securing device via said linear actuator when said image recording unit with said rotation device is rotated about said rotational axis to effect said combined movement about the tilt axis such that a distance between the focal point and said second securing device is kept constant within a predetermined interval; the method comprising:
- defining said focal point of the image recording unit and a focal distance (f);
- defining an initial position of the image rendering unit and of the image recording unit in relation to the connecting rail of the mount and the focal point and determining a distance, emerging therefrom, between the image rendering unit and the focal point;
- tilting the image recording unit through a defined angle ($\alpha$) about a tilt axis extending through the focal point, wherein the image recording unit with said rotation device is rotated about said rotational axis extending parallel to the tilt axis; and,
- moving the connecting rail in a direction extending perpendicularly to the tilt axis in relation to the image rendering unit by one path length on the basis of the focal length and tilt angle ($\alpha$) such that the distance between the image rendering unit and the focal point is kept constant within a predetermined interval.

13. The method of claim 12, wherein at least one of the focal length lies between 1 mm and 300 mm, the tilt angle ($\alpha$) lies between −20 degrees and +50 degrees, and the path length lies between 0 and 300 mm.

\* \* \* \* \*

UNITED STATES PATENT AND TRADEMARK OFFICE
CERTIFICATE OF CORRECTION

| | |
|---|---|
| PATENT NO. | : 11,253,334 B2 |
| APPLICATION NO. | : 17/119916 |
| DATED | : February 22, 2022 |
| INVENTOR(S) | : Mueller et al. |

It is certified that error appears in the above-identified patent and that said Letters Patent is hereby corrected as shown below:

In the Specification

In Column 4:
Line 58: delete "(a)" and insert -- ($\alpha$) -- therefor.

In Column 13:
Line 34: delete "?" and insert -- $\alpha$ -- therefor.

In the Claims

In Column 17:
Line 43: delete "a mount having a connecting rail extending in a y-direction;".

In Column 18:
Line 35: delete "image recording unit and a second securing device for an image".

Signed and Sealed this
Twenty-fourth Day of May, 2022

Katherine Kelly Vidal
*Director of the United States Patent and Trademark Office*